(12) United States Patent
Hilliard

(10) Patent No.: US 6,293,790 B1
(45) Date of Patent: Sep. 25, 2001

(54) HEATED ORTHODONTIC PLIERS

(76) Inventor: J. Keith Hilliard, 330 E. Highland Dr., Lakeland, FL (US) 33813

( * ) Notice: Subject to any disclaimer, the term of this patent is extended or adjusted under 35 U.S.C. 154(b) by 0 days.

(21) Appl. No.: 09/250,271

(22) Filed: Feb. 16, 1999

Related U.S. Application Data

(60) Provisional application No. 60/075,018, filed on Feb. 18, 1998.

(51) Int. Cl.[7] .............................. A61C 3/00; A61C 3/14
(52) U.S. Cl. .............................. 433/4; 433/159; 81/426; 101/3.1
(58) Field of Search ................... 433/4, 159; 81/426, 81/418, 424.5; 101/3.1; D18/15; 400/127, 128

(56) References Cited

U.S. PATENT DOCUMENTS

| | | | |
|---|---|---|---|
| 340,896 | * | 4/1886 | Starr . |
| 634,493 | * | 10/1899 | Bradley . |
| 1,304,720 | * | 5/1919 | Young . |
| 1,316,409 | * | 9/1919 | Bahre . |
| 2,040,749 | * | 5/1936 | Linn . |
| 3,727,316 | | 4/1973 | Goldberg . |
| 3,911,583 | | 10/1975 | Hoffman . |
| 4,070,745 | * | 1/1978 | Schimmelmann ............... 81/426 |
| 4,310,305 | | 1/1982 | Frajdenrajch . |
| 5,011,491 | * | 4/1991 | Boenko et al. ............... 81/418 |
| 5,084,935 | | 2/1992 | Kalthoff . |
| 5,197,880 | | 3/1993 | Lovaas . |
| 5,257,558 | * | 11/1993 | Farzin-Nia et al. ............... 81/418 |
| 5,395,236 | | 3/1995 | Khouri . |
| 5,538,421 | | 7/1996 | Aspel . |
| 5,588,832 | | 12/1996 | Farzin-Nia . |

* cited by examiner

*Primary Examiner*—Ralph A. Lewis
(74) *Attorney, Agent, or Firm*—Richard C. Litman

(57) ABSTRACT

Orthodontic pliers comprised of two asymmetrical components that are subapically and pivotally joined in a first main embodiment. Each of these elongate pieces is irregular in shape, unequal in length and the jaws are asymmetrical jaws relative to each other. The pliers when heated are used for producing or modifying bumps on a thermoplastic retainer. One of the jaws has a throughbore or blind bore for receiving the bump forming end of the other jaw. The jaw with the bump forming end is shorter and curvilinear so that the only part of that jaw that comes in contact with the retainer is the bump forming end. Additionally, the bump forming end may be of different shapes in order to produce different shaped bumps such as ramps, logos, logo pockets, fluoride pockets, bite plates, rectangular shapes for the retention of blocks to be wired, and hooks for elastic banding, depending on the needs of the individual patients. The pliers are heated to a temperature range of approximately 325° F. to 350° F., or the appropriate temperature for a specific thermoplastic material, to facilitate the formation of the bump in the thermoplastic retainer. A second main embodiment includes a system of pliers with jaws of equal and symmetrical shape for crimping a warmed retainer having an encapsulated expansion screw.

4 Claims, 18 Drawing Sheets

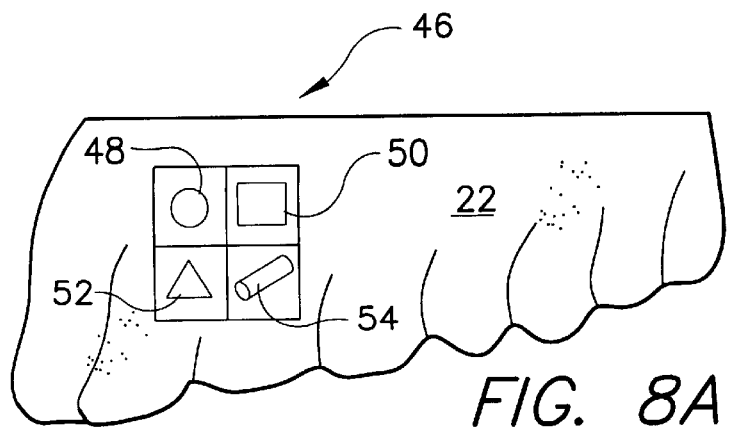
FIG. 8A
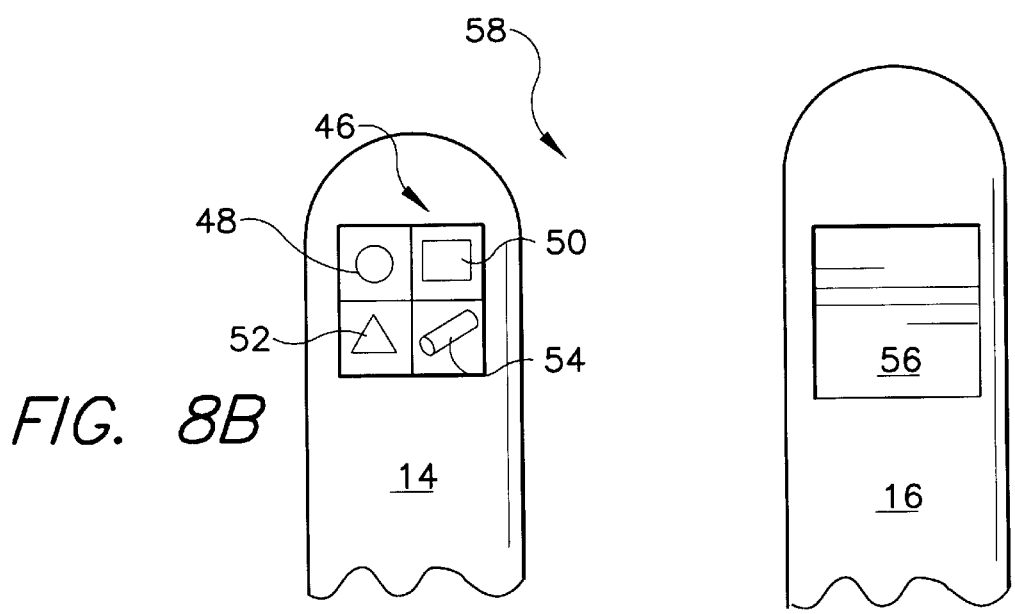
FIG. 8B
FIG. 8C
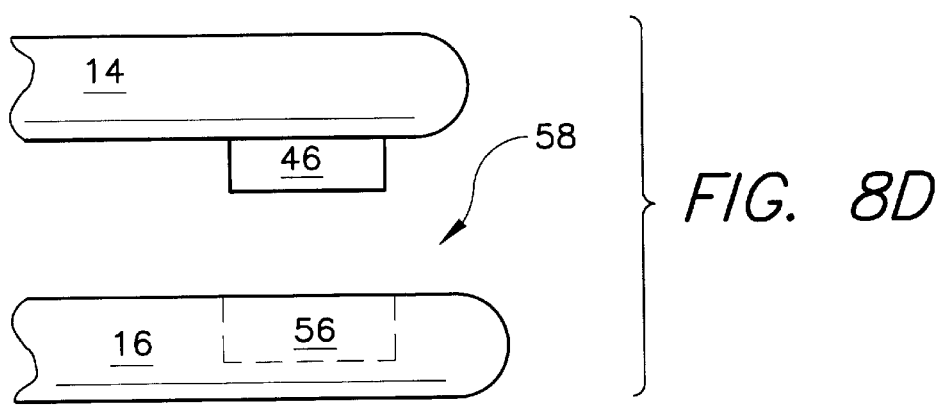
FIG. 8D

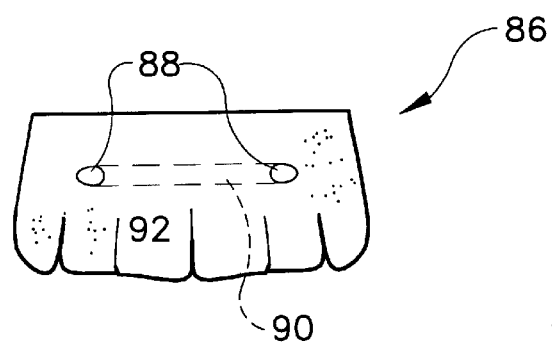
FIG. 11A
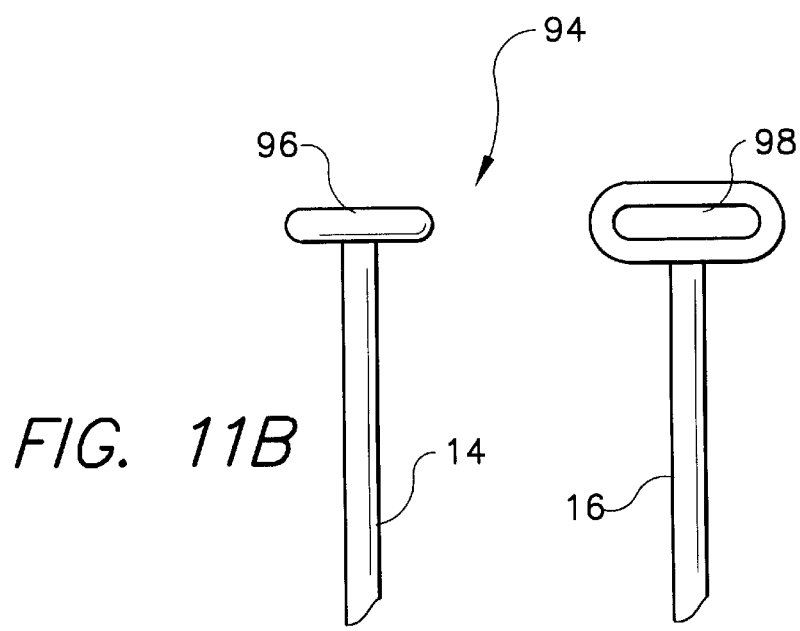
FIG. 11B
FIG. 11C
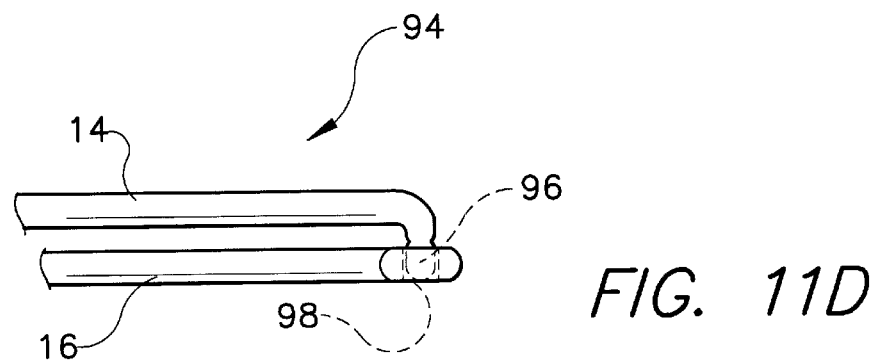
FIG. 11D

HEATED ORTHODONTIC PLIERS

CROSS-REFERENCE TO RELATED APPLICATION

This application claims the benefit of U.S. Provisional Patent Application Ser. No. 60/075,018, filed Feb. 18, 1998.

BACKGROUND OF THE INVENTION

1. Field of the Invention

The present invention relates generally to dental instruments. More specifically, the invention is directed to a plurality of heated orthodontic pliers with jaws having various configurations. The pliers are used for producing various configurations of bumps, logos and cuts on and pinching of a retainer fabricated from thermoplastic co-polymer blends. To achieve this end, the pliers are heated to a sufficiently high temperature and then placed on the retainer to reshape it at a specific location.

2. Description of Related Art

In the field of orthodontics it is useful to form differently shaped bumps and cuts in a thermoplastic retainer in order for the dental retainer to apply appropriate corrective pressure to a patient's teeth. Another problem is the looseness of a fastener incorporated in a retainer. To this point, once the retainers are manufactured, it is difficult for the individual orthodontist to reshape the retainer to meet the changing needs of his patient. Additionally, the only known method of forming these bumps is by using a heated rod that works like a soldering iron to form a cylindrical bump in the retainer. This method is not as effective as the present invention because it can only result in limited forms of bumps. The soldering iron must be heated electrically and works effectively only on specific thermoplastic materials, rather than on all thermoplastic materials as does the present invention.

What is needed is an assortment of orthodontic pliers that are capable of easily and accurately forming different shaped ramps, imprinted logos, logo pockets, fluoride and bleach pockets, bite plates, rectangular shapes for retention of blocks on any thermoplastic retainer and pinching down on loose fasteners when heated to a sufficient temperature. This will allow orthodontists to make the minor modifications that are often necessary in a cost effective manner. A discussion of the related art of which the present inventor is aware, and its differences and distinctions from the present invention is provided below. No patent discloses the necessity to heat the dental pliers for forming bumps or pinching loosely held fasteners in the thermoplastic retainer.

U.S. Pat. No. 5,538,421 issued on Jul. 23, 1996, to Thomas E. Aspel describes an assortment of dental pliers comprising a lower jaw longer or shorter than the upper jaw for removing orthodontic brackets, bands, buttons, cleats, bonding materials, and braces from teeth. The pliers are distinguishable for being limited to jaws designed for cutting and removing unwanted dental materials from the patient's teeth and to prevent luxation (tipping) of the tooth to minimize pain while using the pliers.

U.S. Pat. No. 3,911,583 issued on Oct. 14, 1975, to Robert Hoffman describes a dental pliers having an upper jaw having an upwardly and inwardly tapered concave shaped sides and front for forming gripping edges in removing metal bands cemented to teeth and the removal of cement on teeth. The pliers are distinguishable for being limited to removal of cemented dental bands and cement.

U.S. Pat. No. 5,395,236 issued on Mar. 7, 1995, to Suhail A. Khouri describes an orthodontic pliers for forming a wire on teeth to effect gingivally directed bends in the distal ends of the arch wire. The jaws of the pliers have perpendicular free ends which render the plier structurally distinguishable from the present invention.

U.S. Pat. No. 5,084,935 issued on Feb. 4, 1992, to Ferdinand Kalthoff describes a multiple-purpose wire shaping and cutting tool. It further describes means of forming certain commonly known wire shapes used in the orthodontic profession. There are opposing convex and concave surfaces on its inner jaws in order for the tool to perform its intended function. One handle has a hole while the other handle has a disc-shaped guide for forming labial bows in a wire. The wire shaping tool is distinguishable for lacking any means of forming shapes in thermoplastic retainers, nor is there disclosure of any heating of the tool to facilitate wire formation.

U.S. Pat. No. 3,727,316 issued on Apr. 17, 1973, to Louis Goldberg describes an orthodontic pliers used for bending wire into desired open or closed loop sizes, and for forming and modifying the arch curve in the wire. The pliers possess male and female conical dies (including a recess on one jaw) and a wire cutter on opposing surfaces of the inner jaws. No means of heating the pliers or use of the pliers on thermoplastics is disclosed in Goldberg. The orthodontic pliers are distinguishable for its limitation to manipulating and cutting wire.

U.S. Pat. No. 5,197,880 issued on Mar. 30, 1993, to Leeland M. Lovaas describes a tool for crimping a metal endodontic file. The tool has opposing convex and concave surfaces on its inner jaws to perform its intended function. Unlike the present invention, the inner surfaces of the jaws are parallel to one another when the tool is in its closed position. The file crimping tool of FIG. 8 is distinguishable because the tool cannot be used for the formation of bumps in thermoplastic retainers.

U.S. Pat. No. 4,310,305 issued on Jan. 12, 1982, to Jacob Frajdenrajch describes a mechanical device for holding elastic articles such as small orthodontic rubber bands. One embodiment of the invention describes the device having jaws which are curved at their ends to facilitate the use of the device in tight spaces. The orthodontic tool does not suggest the use of the curved-jaw device for imparting pressure on a thermoplastic surface. Additionally, the curved jaw assembly is structurally unlike that of the present invention.

U.S. Pat. No. 5,588,832 issued on Dec. 31, 1996, to Farrokh Farzin-Nia describes a method of fabricating orthodontic pliers and the stainless steel or titanium alloy pliers made by the process. The manufacturing process of making these pliers minimizes the grinding and cutting of the pliers once the two nearly identical halves are made into the two scissor parts. The orthodontic pliers are distinguishable for having conventional needle-nose jaws.

None of the above inventions and patents, taken either singly or in combination, is seen to describe the instant invention as claimed.

SUMMARY OF THE INVENTION

The present invention is a heated orthodontic pliers comprising two components in a first embodiment that are subapically and pivotally joined. Each of these elongated pieces are irregular in shape, unequal in length and possess asymmetrical jaws relative to each other. The lower jaw of one plier is curved in an arc to ensure that the only part of the lower jaw of the plier that comes in contact with the thermoplastic retainer is the bump forming end of that jaw when the jaws are closed around the retainer. The heated pliers are used for producing different shaped bumps on a thermoplastic retainer. A second embodiment of pliers have equal length jaws for different purposes such as tightening the retainer about its fittings enclosed or otherwise.

To achieve the shaping of retainers, the pair of pliers are heated to a temperature range of approximately 325 to 350° F. or the appropriate softening temperature for a specific thermoplastic material, and then placed on the retainer to reshape it. It is noted that the orthodontist will wear insulated gloves when handling the heated pliers. The reshaping end of the lower jaw of the pliers can be shaped in various ways so that it will create a smooth, evenly shaped bump in the retainer that is comfortable for the patient to wear. After the bumps are created, the retainer is permitted to cool and stabilize, i.e., harden. The specially reshaped retainer may then be placed in the patient's mouth to impart corrective pressure to the desired tooth. The various configured shapes formed by the specific orthodontic pliers of the present invention are an elliptical bump, a square bump, a rectangular bump, a tear shaped bump, ramps of different sizes, circular and square logos, logo attaching apertures, fluoride and bleach pockets, horizontal and vertical hooks, a biteplate, and square or rectangular bumps for inserting blocks for connecting the blocks with wires, tubes, elastic chains, and springs. Other uses include specially configured pliers with heated jaws of equal length for crimping encapsulated expansion screws or the like.

Accordingly, it is a principal object of the invention to provide a pair of orthodontic pliers for the purpose of accurately forming bumps or pinching loosely encapsulated fasteners in thermoplastic retainers when the pliers are sufficiently heated to a temperature range of approximately 325 to 350° F. or the appropriate softening temperature for a specific thermoplastic material.

It is another object of the invention to be able to form the bumps of different shapes on the retainer, depending on the specific needs of the patient, by changing the shape of the bumpforming end of the jaws of the pliers having unequal length.

It is a further object of the invention to crimp encapsulated expansion screws and the like in thermoplastic retainers that make the retainer comfortable for the patient to wear with heated pliers having jaws of equal length but different configurations.

It is still another object of the invention to provide an assortment of orthodontic pliers with unequal jaw length which will provide various configured shapes as an elliptical bump, a square bump, a rectangular bump, a tear shaped bump, ramps of different sizes, circular and square logos, logo retaining apertures, fluoride pockets, horizontal and vertical hooks, a bite-plate, and square or rectangular bumps for inserting blocks for connecting the blocks with wires, tubes, elastic chains, and springs.

It is an object of the invention to provide improved elements and arrangements thereof in an orthodontic tool for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 8A is an elevational side view of a thermoplastic retainer depicting the logo impressed on it by a logo pliers of a fifth embodiment.

FIG. 8B is a partial plan view of the underside of the upper jaw of the pliers of the fifth embodiment.

FIG. 8C is a partial plan view of the underside of the lower jaw of the pliers of the fifth embodiment.

FIG. 8D is a partial elevational side view of the jaws of the pliers of the fifth embodiment.

FIG. 11A is a front elevational view of a thermoplastic retainer with a pair of horizontal hooks for an elastic band oriented to open outwardly and made initially by ramps formed by a pliers of the eighth embodiment.

FIG. 11B is a partial plan view of the underside of the upper jaw of the horizontal hook forming pliers of the eighth embodiment.

FIG. 11C is a partial plan view of the underside of the lower jaw of the horizontal hook forming pliers of the eighth embodiment.

FIG. 11D is a partial side elevational view of the closed jaws of the eighth embodiment pliers.

FIG. 12B is a partial plan view of the underside of the upper jaw of the ninth embodiment pliers.

FIG. 12C is a partial plan view of the underside of the lower jaw of the ninth embodiment pliers.

Similar reference characters denote corresponding features consistently throughout the attached drawings.

DETAILED DESCRIPTION OF THE PREFERRED EMBODIMENTS

Figure 1:
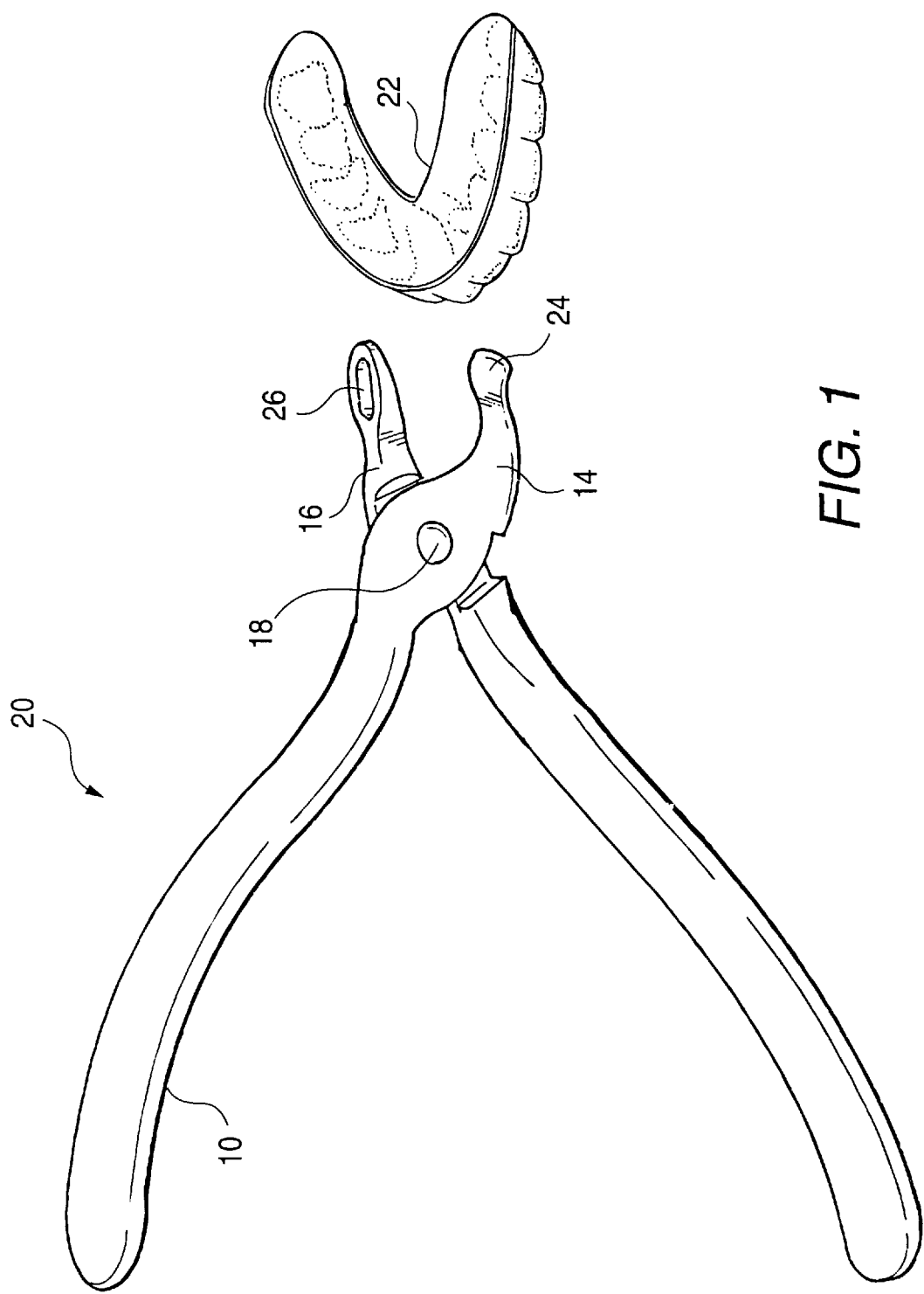
FIG. 1 is an environmental, perspective view of a first embodiment of an orthodontic pliers for forming a bump and a thermoplastic retainer according to the present invention.

The present invention is a heated pair of orthodontic pliers used for forming bumps in thermoplastic retainers. In the field of orthodontics, a retainer is generally individually produced to fit an patient's mouth. However, over time a patient's needs may change, thus making it is necessary to slightly modify the retainers. The generic components of an orthodontic plier typically comprise a first handle 10 having a first jaw 14, a second handle 12 having a second jaw 16, which are subapically and pivotally joined by a pivot pin 18 connecting the handle and jaw assembly, as suggested by FIG. 1, which is drawn to a first embodiment pliers 20 of the present invention. A thermoplastic retainer 22 is illustrated ready for bump formation by a bump forming projection 24 of the first jaw 14 which pushes the pertinent portion of the retainer 22 into the elliptical throughbore 26 of the second jaw 16.

Figure 2:
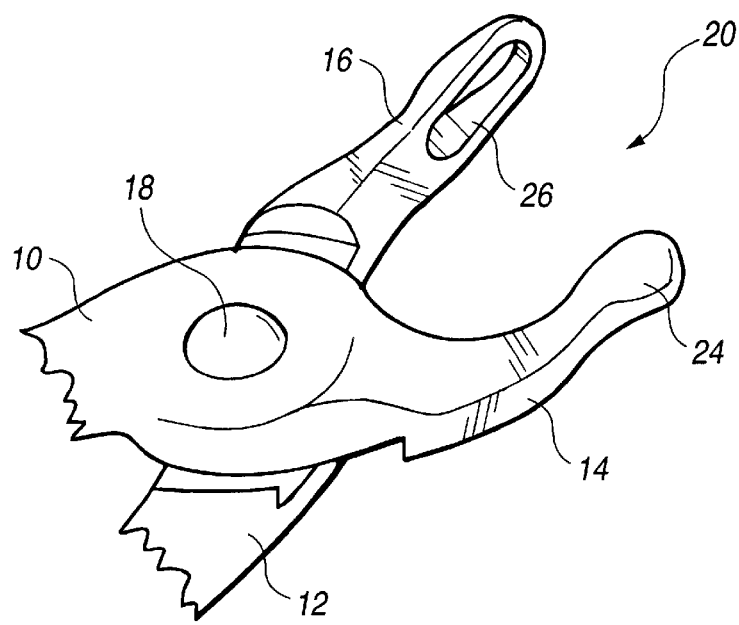
FIG. 2 is a partial perspective view of the FIG. 1 pliers in an open position.
Figure 3:
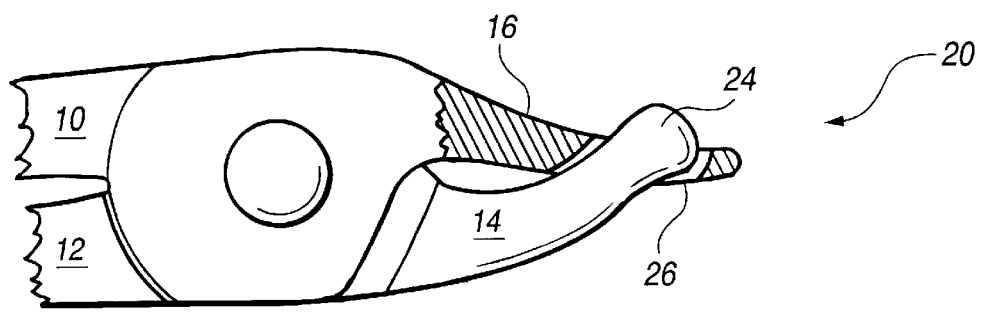
FIG. 3 is a partial side elevational view of the jaws of the FIG. 1 pliers in a closed position with the apertured jaw partially cross-sectioned to demonstrate the manner in which the jaws fit together.
Figure 4:
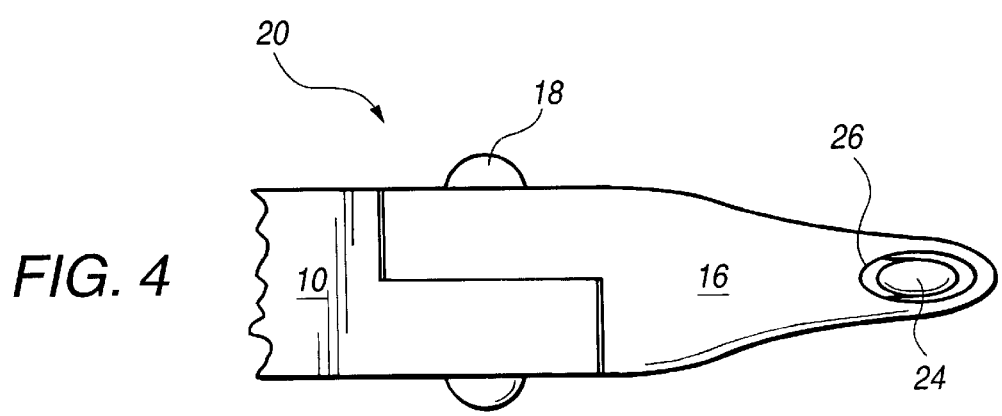
FIG. 4 is a top plan view of the jaws of the FIG. 1 pliers.

As shown in FIGS. 2, 3 and 4, the first jaw 14 is curved to ensure that the only part of the first jaw 14 that comes in contact with the thermoplastic retainer 22 is the bump forming projection 24 of the first jaw 14 when the jaws are closed around the retainer 22. It should be noted that the space between the bump forming projection 24 and the elliptical throughbore 26 shown in FIG. 4 would be the thickness of the bump in the retainer 22.

The bump forming projection 24 of the first jaw 14 can be shaped differently depending on the shape that the orthodontist wants to create in the retainer. Alternatively, the shape of the elliptical throughbore 26 can be teardrop shaped (not shown) to create a smooth surfaced ramp (similar to ramps shown in FIGS. 6 and 13C) in the thermoplastic retainer 22 which imparts even pressure to the appropriate tooth and is comfortable for the patient to wear. The teardrop shape allows for a gradation of corrective pressure to be imparted to the desired tooth as the patient bites down. The teardrop throughbore can be inverted to apply the same sort of varying pressure as the teardrop. However, the inverted teardrop faces in a diametrically opposite direction than the teardrop of the above embodiment in order to account for the orthodontic needs of different patients.

Figure 5:
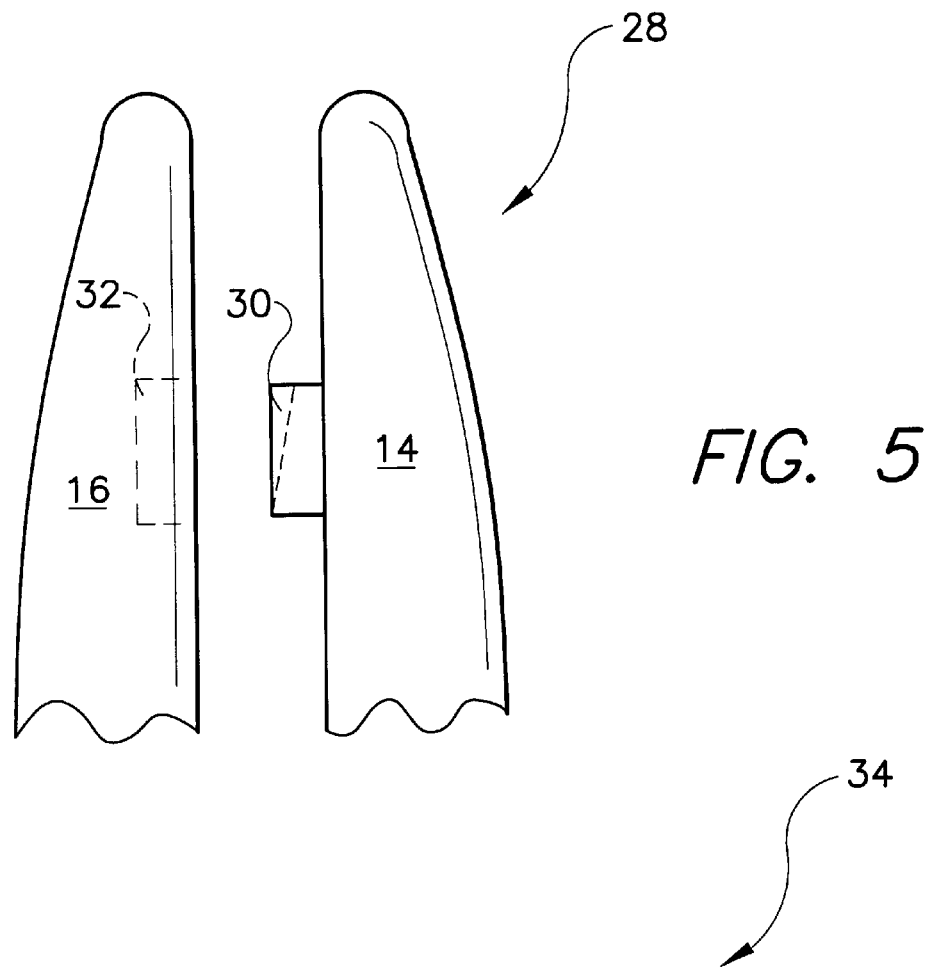
FIG. 5 is an elevational side view of the jaws of a second embodiment of a pliers for increasing an undercut in a thermoplastic retainer.

A second embodiment directed to an undercut increasing orthodontic plier 28 is illustrated in FIG. 5 with a first jaw 14 having a square shaped projection 30 and a second jaw 16 having a square shaped blind bore 32 with a slightly larger size to accommodate the retainer 22 being shaped to form the undercut. The purpose of using this plier 28 is to increase the undercuts in the thermoplastic overlay retainer. The significance of increasing the undercuts is that the undercut holds the overlay retainer on the teeth. The increased retention prevents the retainer from being easily dislodged. There are situations where additional retention over and above that available from the plaster work model that the retainer is made from would be advantageous to the wearer.

Figure 6:
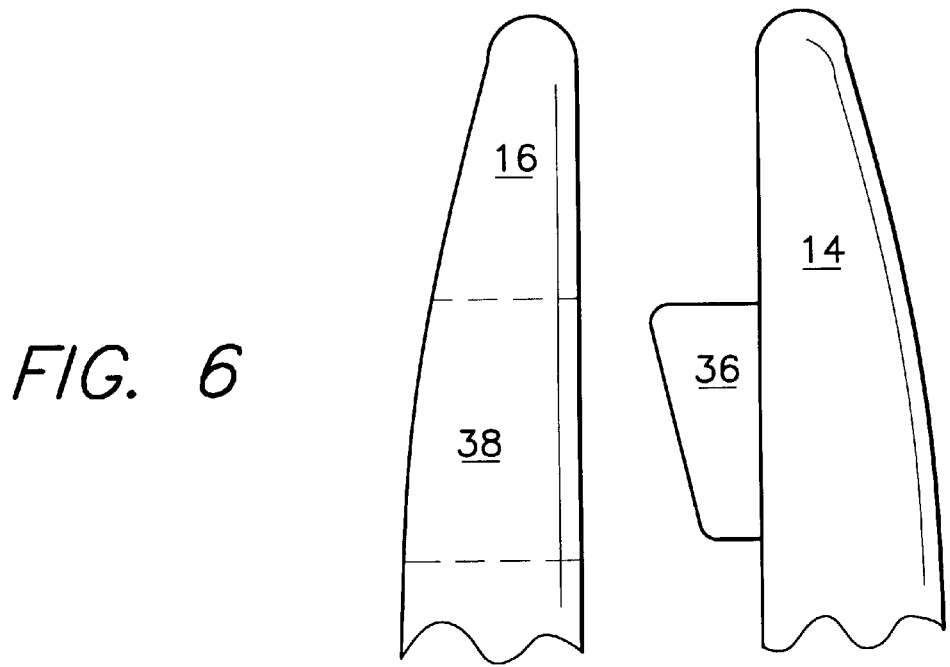
FIG. 6 is a partial elevational side view of the jaws of a third embodiment of a smaller ramp forming pliers required for the lower anterior teeth portion of a thermoplastic retainer.

In FIG. 6, a small ramp plier 34 is shown as a third embodiment for use on the lower anterior teeth in the retainer 22, as the anterior teeth are smaller on the lower jaw than in the upper jaw. Thus, the ramp 36 has a longer projection 37 (nearest the end of the jaw 12), which when heated pushes the warmed retainer portion through a throughbore 38, sized to exceed the dimensions of the ramp 36, to form a correspondingly shaped ramp projection in the retainer 22.

Figure 7A:
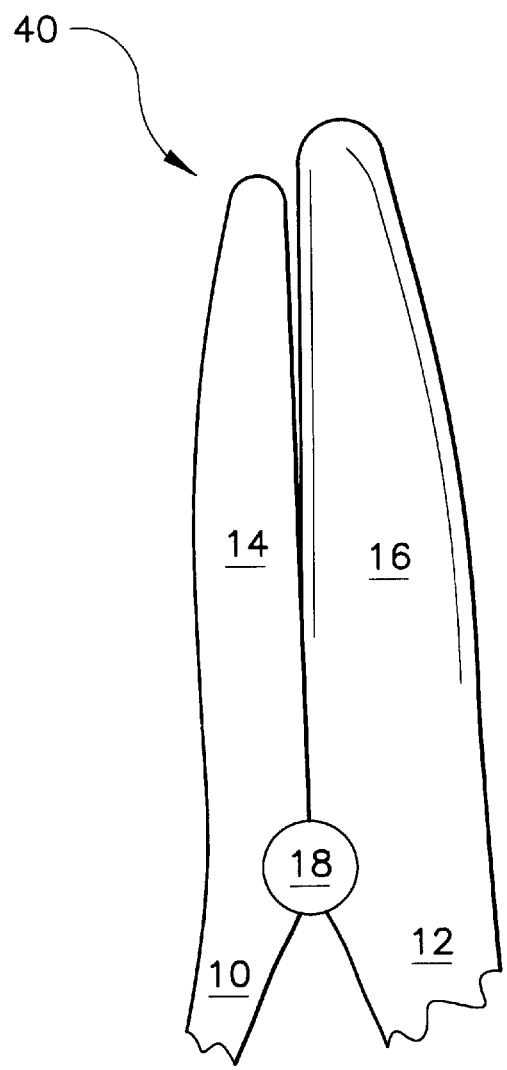
FIG. 7A is a partial elevational side view of the jaws of a fourth embodiment of a pliers for reducing the size of an oversized ramp in a thermoplastic retainer.
Figure 7B:
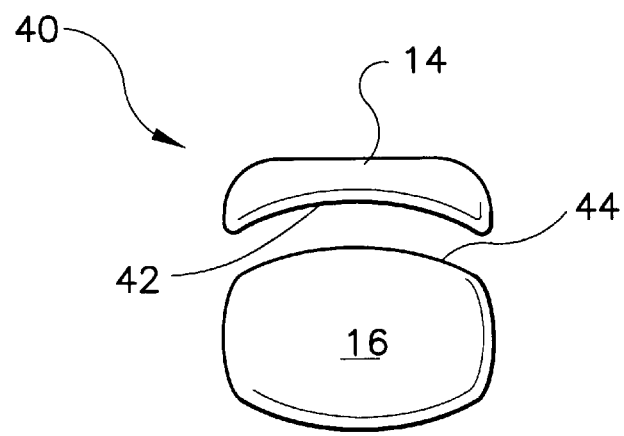
FIG. 7B is an elevational front end view of the jaws of the FIG. 7A embodiment.

FIGS. 7A and 7B are directed to a fourth embodiment of an orthodontic plier 40 designed for reducing the size of an oversized ramp in a thermoplastic retainer. The oversized ramp may be pushing a tooth too far out of alignment, or, may be determined by the clinician to have been formed in the laboratory too large for proper fit and placement in the patient's mouth. Plier 40 has a shorter first jaw 14 with a slightly concave, cross-sectional surface 42 which is inserted inside the retainer 22 and which cooperates with a slightly convex, cross-sectional surface 44 of the second jaw 16, placed against the outside the retainer 22. The use of pliers 40 results in the saving of a new retainer.

In FIGS. 8A, 8B, 8C, and 8D, a fifth embodiment of the invention is shown, wherein the bump forming end is shaped to provide an identification means on the retainer, either on the outside surface as shown, or alternatively, on the inside surface. For example, the shape can be that of a logo of a company or an ornamental design. In FIG. 8A, the square logo 46 with four equal sized segments on the outside of a retainer 22 consists of a decorative design of a circle 48, a rectangle 50, a triangle 52, and a cylinder 54. In FIG. 8B, the pliers 58 have the shorter first jaw 14 defining a protruding block 47 including raised or depressed features of logo 46. In FIG. 8C, the longer second jaw 16 has a square blind bore 56 of slightly greater dimensions than that of the block 47 to receive the front portion of the thermoplastic retainer receiving the logo impression.

In FIGS. 9A, 9B, 9C, 9D, and 9E, a sixth embodiment of the invention shows a retainer 60 (FIG. 9A) with a circular logo insert 61 held in a circular cutout 62 made within a circular rimmed retention area 63 which was formed by a circular bump forming pliers 64 (FIG. 9E), wherein the male jaw 14 has a circular ridge 65 at the end of the projection 66 which cooperates with the circular throughbore 67 in the female jaw 16.

Figure 9A:
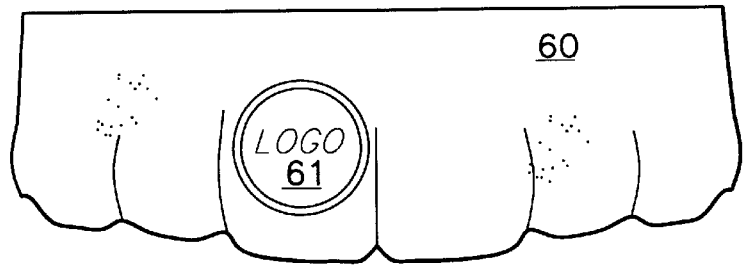
FIG. 9A is a front elevational view of a thermoplastic retainer with a logo insert in a holder made by a circular logo pliers of a sixth embodiment.
Figure 9B:
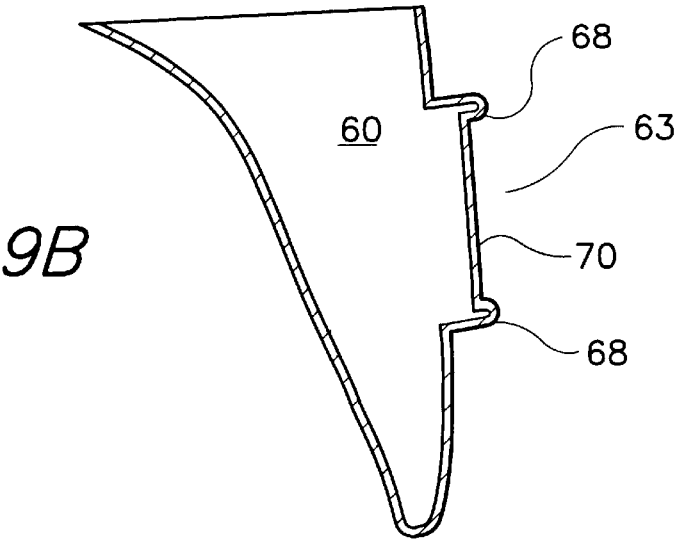
FIG. 9B is a sectional elevational view of the thermoplastic retainer with the configuration made with the circular logo pliers of the sixth embodiment.
Figure 9C:
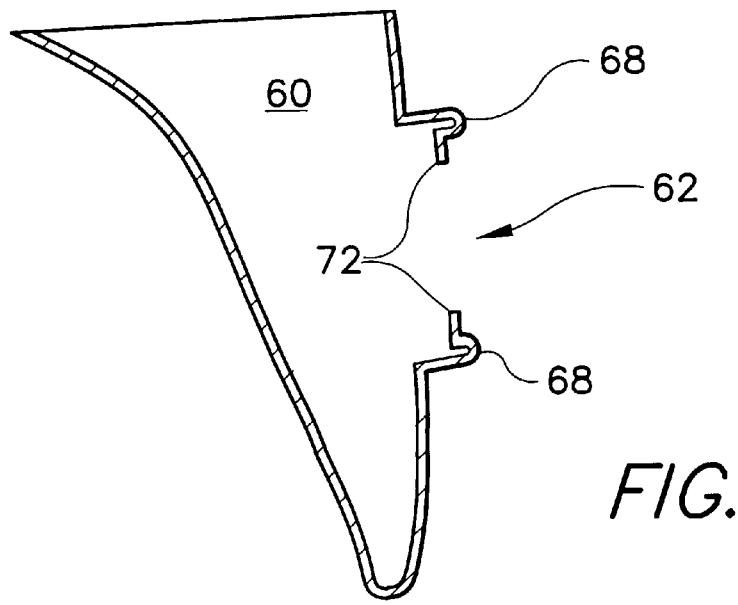
FIG. 9C is a sectional elevational view of the thermoplastic retainer with a hole made with a puncher of a smaller diameter than the circular bump with the pliers of the FIG. 9B embodiment.
Figure 9D:
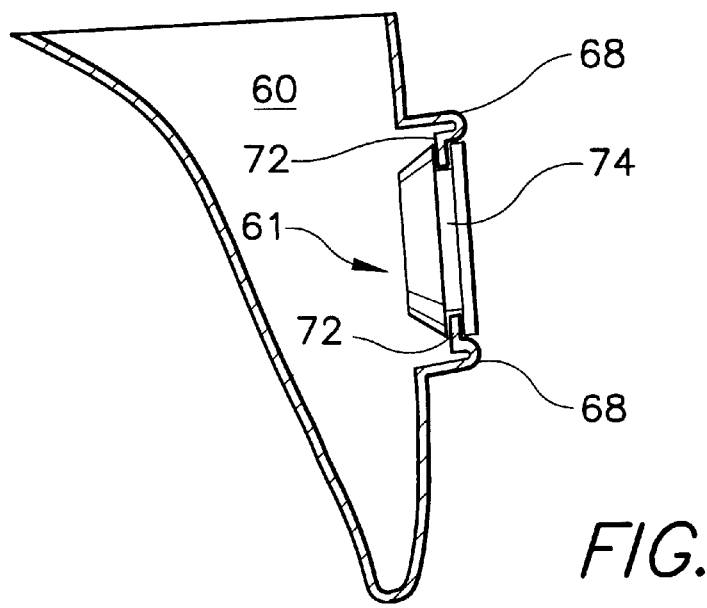
FIG. 9D is a sectional elevational view of the thermoplastic retainer with a logo insert in place in the sixth embodiment.
Figure 9E:
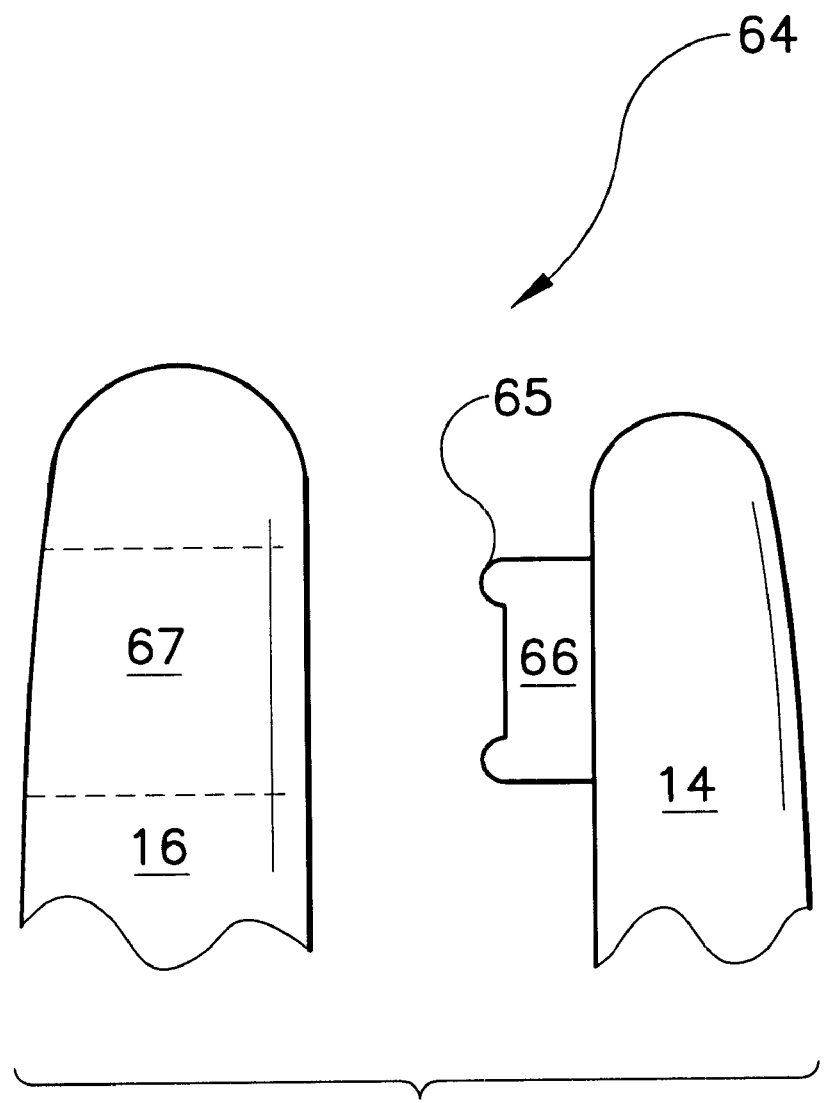
FIG. 9E is a partial side elevational view of the jaws of the circular logo forming pliers of the sixth embodiment.

In FIG. 9B, shows a sectional profile of the thermoplastic retainer 60 showing the rim 68 formed by a peripheral ridge 65 on the male bump 66 of the male jaw 14 being inserted in the throughbore 67 of the female jaw 16 (FIG. 9E). A specially made punch (not shown) can be used to punch out a circle having a diameter less than the depression 70 to form the internal circular flange 72 (FIG. 9C) required to cooperate with the recess 74 in the circular logo insert 61 to retain the insert in the retainer 60 as shown in FIG. 9D.

The indicia 68 shown as "LOGO" in FIG. 9A, is representative of a plurality of items such as the patient's name, company logos, or ornamental designs. Ornamental designs can be any color, plastic or metal, or glow in the dark material. This design allows an otherwise bland clear retainer 60 to be decorated in a way that will be pleasing to pre-teenagers and teenagers. A version of this design will allow the patient to change the colors as they wish to match one's mood, fashion, or for a special occasion. The logo insert does not interfere with the functioning of the retainer 60 and does not make the retainer uncomfortable.

Figure 10A:
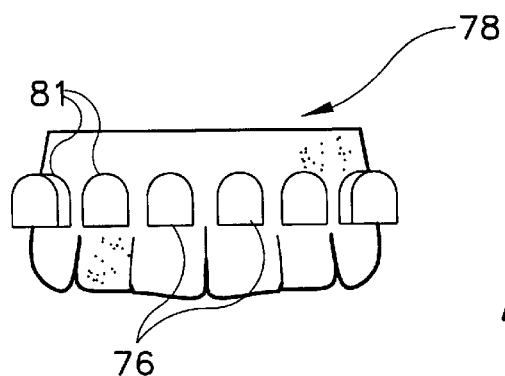
FIG. 10A is a front elevational view of the thermoplastic retainer provided with fluoride pockets made by the pliers of a seventh embodiment.

In FIG. 10A, a thermoplastic retainer 78 containing a plurality of fluoride pockets 76 made by a pocket forming pliers 80 of a seventh embodiment is illustrated. The pockets 76 are formed to contain a fluoride paste and have a circular shaped top portion 81 to follow the outline of the gingiva (gums) and cover the upper third region of the enclosed tooth. The reason for adding fluoride is for treating etched areas of the tooth enamel to replace lost calcium oxide molecules with fluoride molecules. The pocket depth can vary from 1 to 4 mm.

Figure 10B:
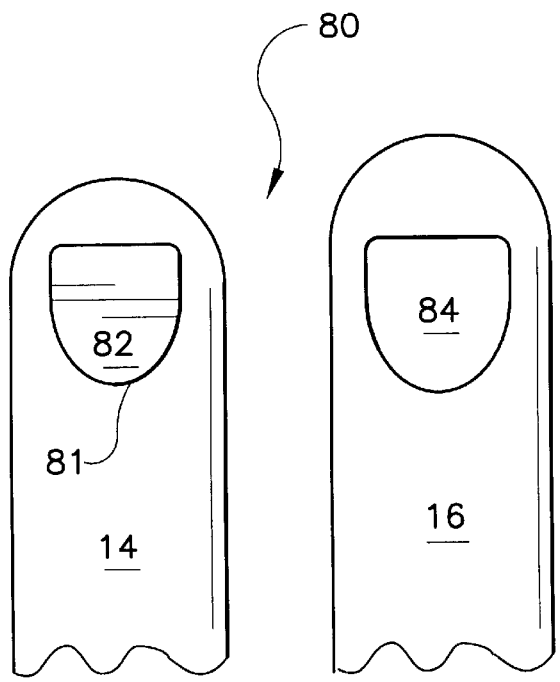
FIG. 10B is a partial plan view of the underside of the upper jaw of the fluoride pocket forming pliers of the seventh embodiment.
Figure 10C:
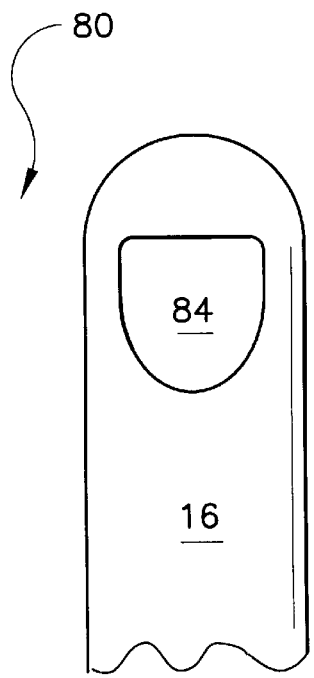
FIG. 10C is a partial plan view of the underside of the lower jaw of the fluoride pocket forming pliers of the seventh embodiment.
Figure 10D:
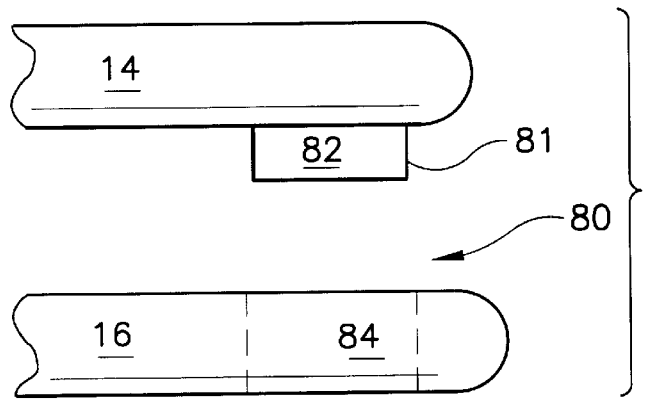
FIG. 10D is a partial elevational side view of the open jaws of the pliers of the seventh embodiment.
Figure 12A:
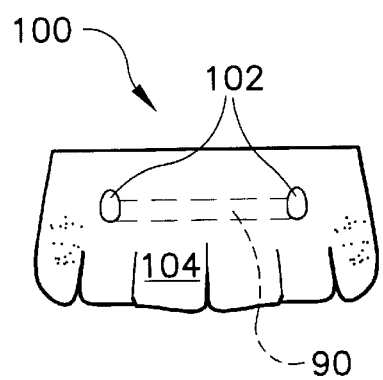
FIG. 12A is a front elevational view of a thermoplastic retainer with a pair of vertical hooks open upwardly for attaching an elastic band; and the ramps made initially formed by a pliers of a ninth embodiment.
Figure 12D:
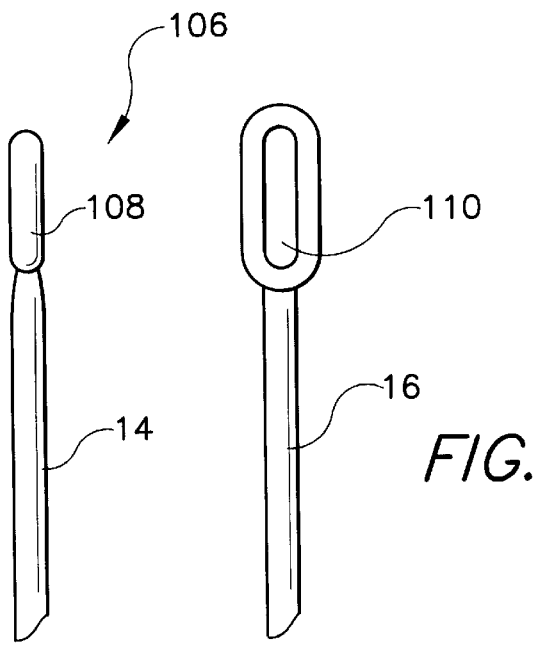
FIG. 12D is a partial elevational side view of the closed jaws of the ramp forming pliers of the ninth embodiment.
Figure 12D:
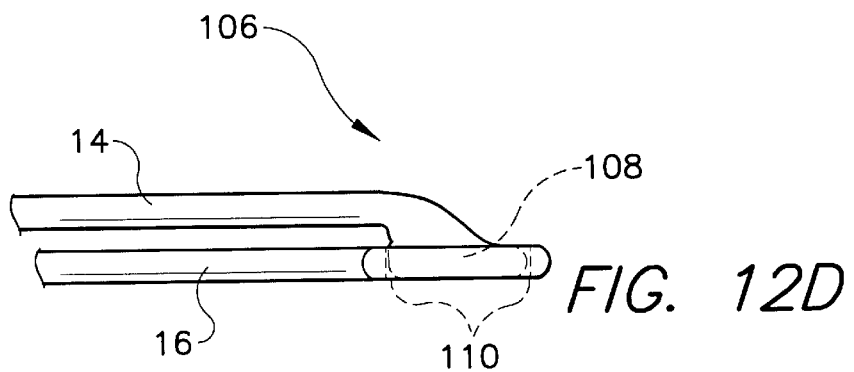

FIGS. 10B and 10C depict the undersides of the jaws 14 and 16, respectively, of the pocket forming pliers 80 showing the pocket projection 82 in jaw 14 and the pocket shaped throughbore 84 in jaw 16.

In FIGS. 11A, 11B, 11C, and 11D, a horizontal hook forming embodiment 86 (eighth embodiment) is illustrated to provide hooks 88 oriented horizontally and opened in opposite positions for attaching an elastic band 90 horizontally (in shadow) on a retainer 92. The horizontal hook forming pliers 94 have a shorter male first jaw 14 with an elongated perpendicular projection 96 at its end perpendicular to the longitudinal axis of the jaw. The female second jaw 16 has an elongated throughbore 98 at its end having an adequate space provided for the portion of the retainer 92 being bumped. The male projection 96 is bent downward at a right angle to the male first jaw 14 to align with the throughbore 98. The pair of elliptical shaped bumps or hooks 88 are opened up on outside edges by a dental drill for accommodating the elastic band 90 in a horizontal position.

Similarly, FIGS. 12A, 12B, 12C, and 12D illustrate a vertical hook forming embodiment 100 (ninth embodiment) to provide vertically oriented hooks 102 open upwards by subsequent cutting of the top surface for attaching an elastic band 90 (in shadow) on a retainer 104. The vertical hook forming pliers 106 have a shorter male first jaw 14 with an elongated projection 108 at its end and a female second jaw 16 with an elongated throughbore 110 at its end having space provided for the portion of the retainer 104 being bumped. The male projection 108 is formed at a right angle to the male first jaw 14.

Figure 13A:
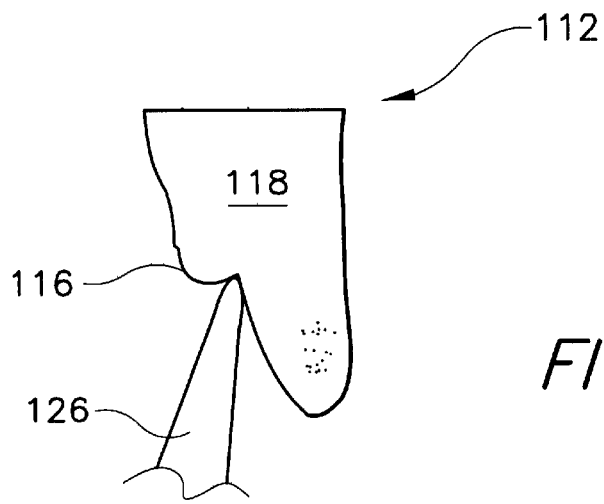
FIG. 13A is an elevational side view of a bite-plate portion of a thermoplastic retainer shown schematically positioned on a lower tooth; the bite-plate portion made by a bite-plate forming pliers of the tenth embodiment.
Figure 13B:
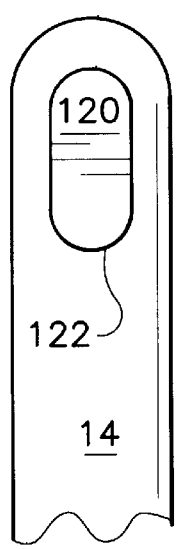
FIG. 13B is a partial plan view of the underside of the upper jaw of the tenth embodiment pliers.
Figure 13C:
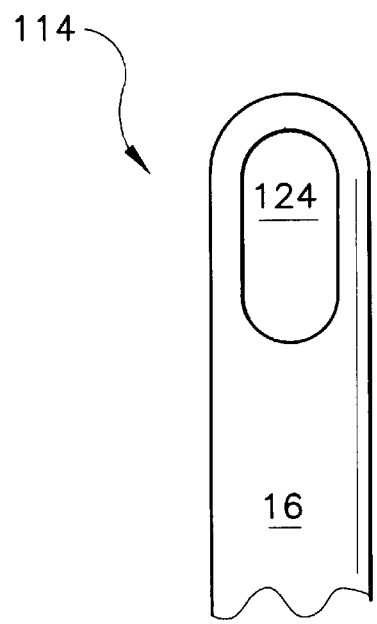
FIG. 13C is a partial plan view of the underside of the lower jaw of the tenth embodiment pliers.
Figure 13D:
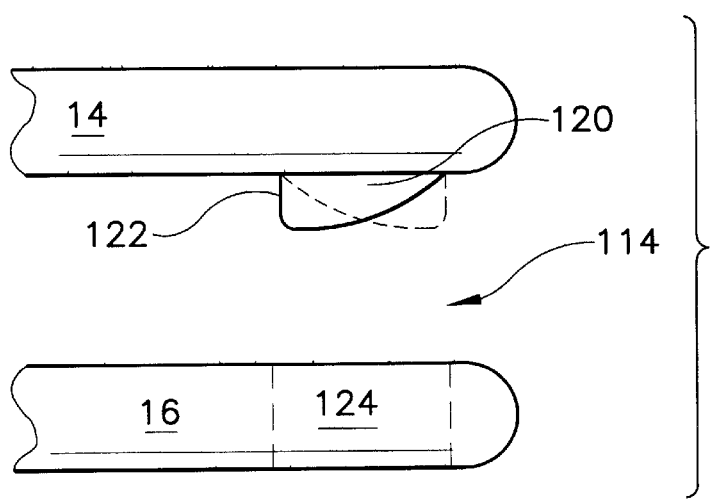
FIG. 13D is a partial elevational side view of the open jaws of the bite-plate forming pliers of the tenth embodiment.

In FIGS. 13A, 13B, 13C, and 13D, a tenth embodiment 112 of the invention shows a bite-plate forming pliers 114 for forming a horizontal ledge or bump 116 in a rear portion of a retainer 118. As shown in FIG. 13B, the forming end or projection 120 of the shorter first jaw 14 is ramp shaped and has an inner surface 122 that extends perpendicular to the horizontal surface of the jaw 14 (FIG. 13D), such that it forms a horizontal ledge or bump 116 in the retainer 118 (FIG. 13A) when the pliers 114 are closed thereon in cooperation with the elongated throughbore 124 in jaw 16 (FIG. 13C). The horizontal ledge 116 provides a surface against which the lower teeth 126 can rest at some distance away from the tongue side of the upper front teeth.

Figure 14A:
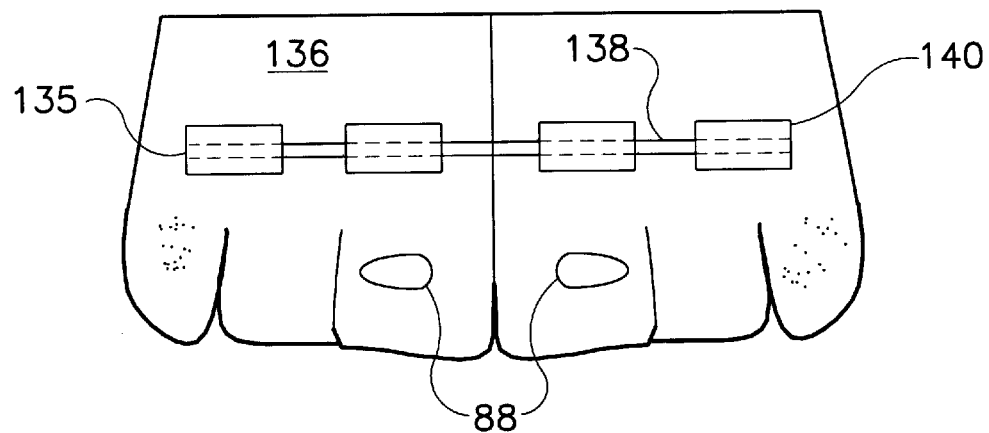
FIG. 14A is an elevational front view of a thermoplastic retainer formed in two sections but joined by horizontally positioned wires, elastic chains, tubes and/or springs in blocks inserted in the rectangular or square receptacles made by the pliers of an eleventh embodiment.
Figure 14B:
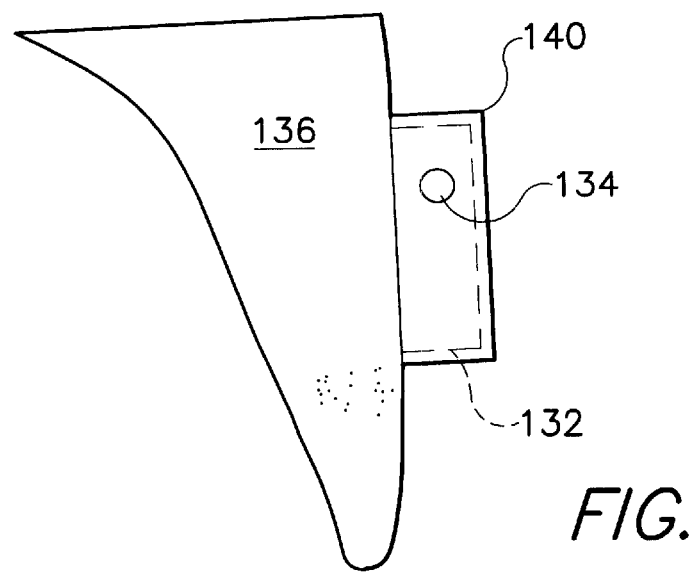
FIG. 14B is a schematic side view of a portion of a thermoplastic retainer impressed with the rectangular or square receptacle containing a horizontally apertured block in the eleventh embodiment.
Figures 14C, 14D:
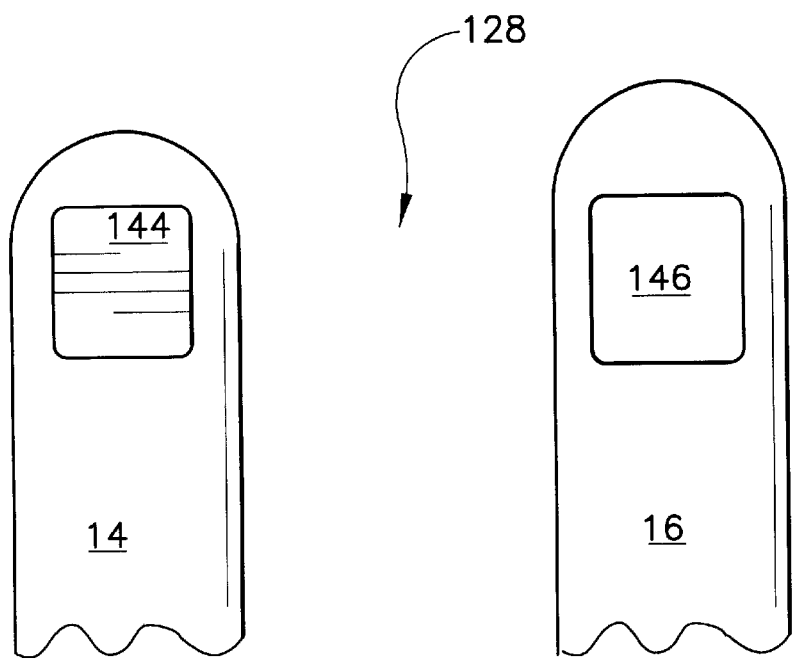
FIG. 14C is a partial plan view of the underside of the upper jaw of the eleventh embodiment pliers.
FIG. 14D is a partial plan view of the underside of the lower jaw of the eleventh embodiment pliers.
Figure 14E:
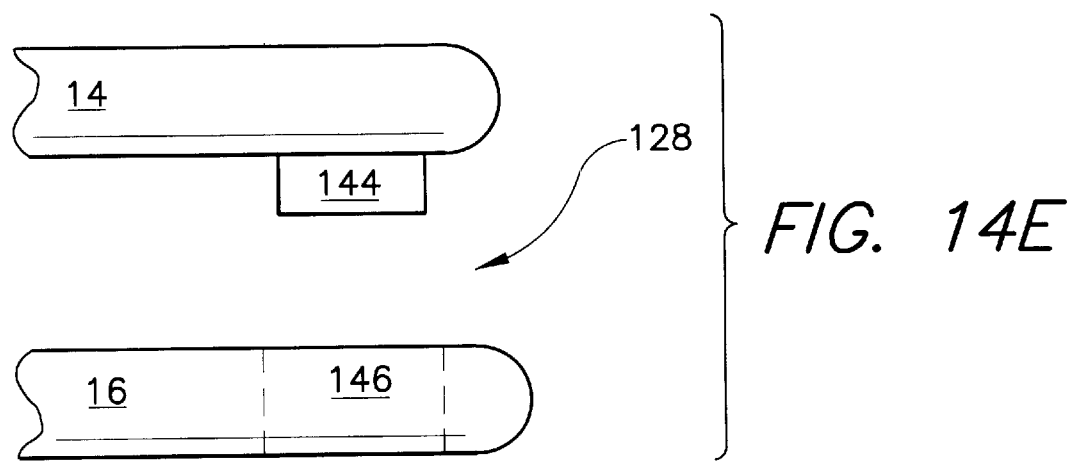
FIG. 14E is a partial elevational side view of the open jaws of the pliers of the eleventh embodiment.

In FIGS. 14A, 14B, 14C, and 14D, a square or rectangular bump forming pliers 128 of an eleventh embodiment forms bumps 140 for the optional inclusion of metal or plastic blocks 132 with throughbores 134 for supporting other orthodontic fasteners such as elastic bands, wires, tubes or springs. The bumps 140 can be left unfilled with apertures 135 made in its sides as shown in FIG. 14A. A retainer 136 formed from two halves is shown with wires 138 connecting the rectangular bumps 140. Two horizontal hooks 88 are shown as a further securement by attaching an elastic band (not shown). In FIG. 14B, a block 132 is shown in shadow inside with a throughbore 134 through the block and the bump 140. of the longer second jaw 16 (FIGS. 14D and 14E) to form the bump 140. Subsequently, a dental drill can form apertures 134 in the bumps 140 and the blocks 132 for attachment of the various aforementioned tensioning agents.

Figure 15:
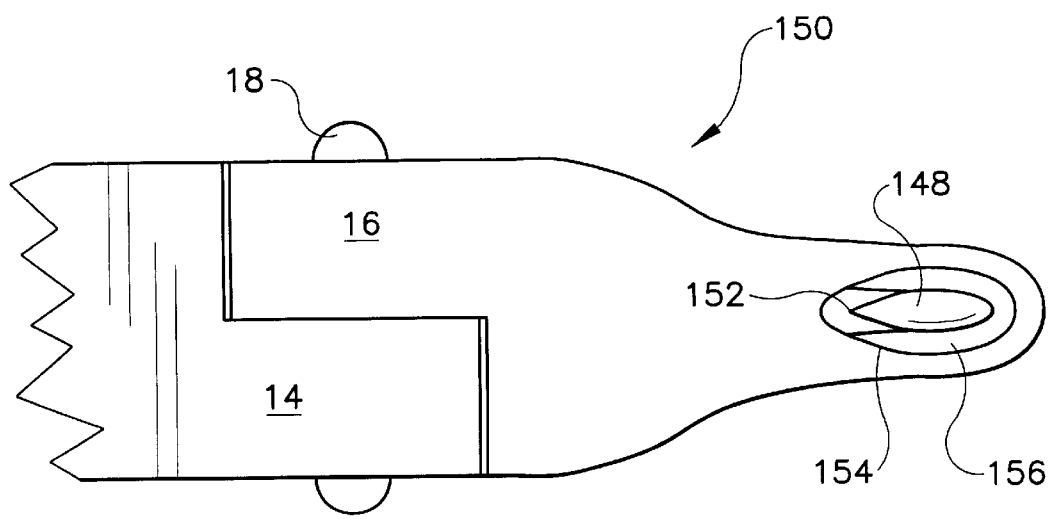
FIG. 15 is a partial plan view of a teardrop forming pliers in a closed position of a twelfth embodiment.
Figure 16:
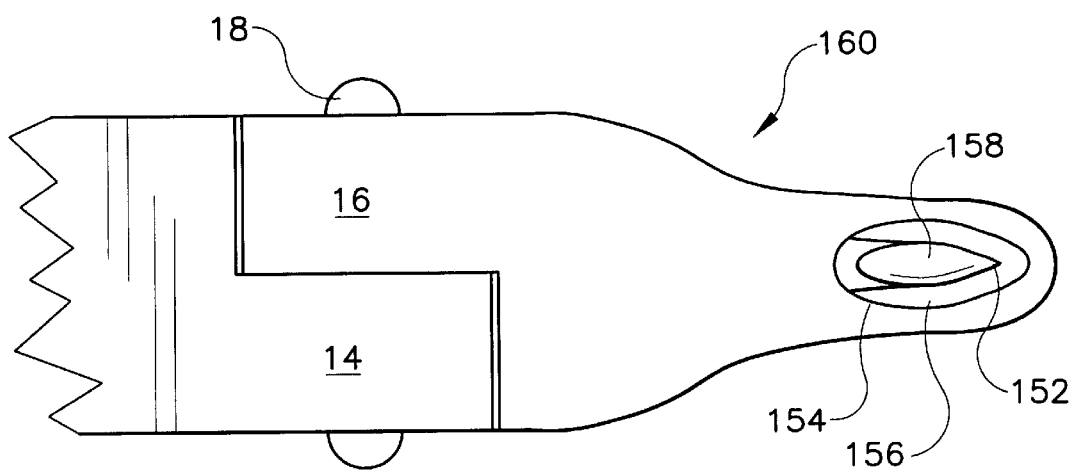
FIG. 16 is a partial plan view of an inverted teardrop forming pliers in a closed position of a thirteenth embodiment.

FIGS. 15 and 16 are drawn to a twelfth embodiment of forming teardrop bumps in a thermoplastic retainer to individually fit a patient's mouth more efficiently. In FIG. 15, the teardrop bump 148 of the shorter jaw 14 of the orthodontic pliers 150 has its pointed end 152 directed inward in the pliers. The throughbore 154 of the jaw 16 is similarly shaped but allows space 156 for the heated thermoplastic retainer. FIG. 16 depicts an inverted teardrop bump 158 forming pliers 160 with the point directed outward. It should be noted that these pliers as others can be utilized with either jaw 14 or 16 inside the retainer to produce a desired conforming bump.

Figure 17A:
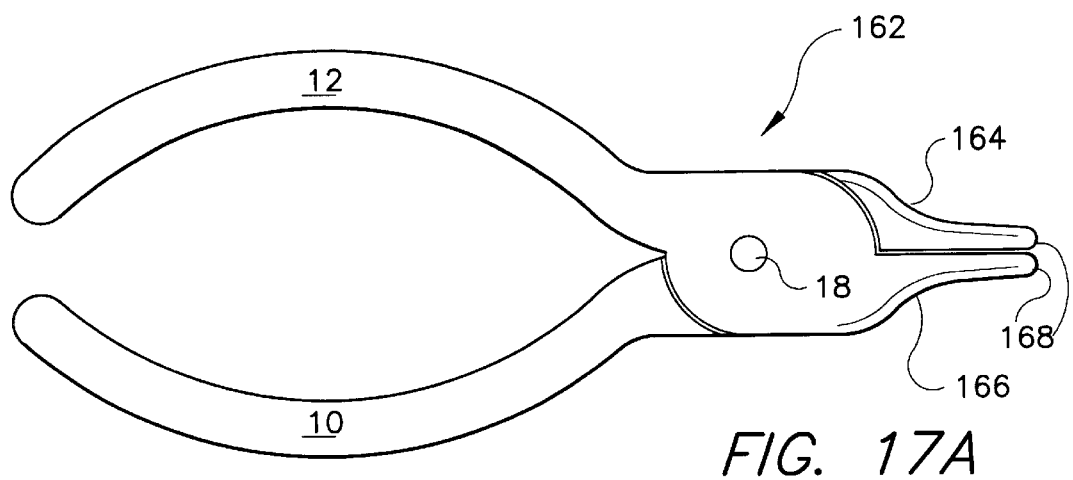
FIG. 17A is an elevational side view of a "dolphin" beaked pliers for crimping encapsulated fasteners of a fourteenth embodiment.
Figure 17B:
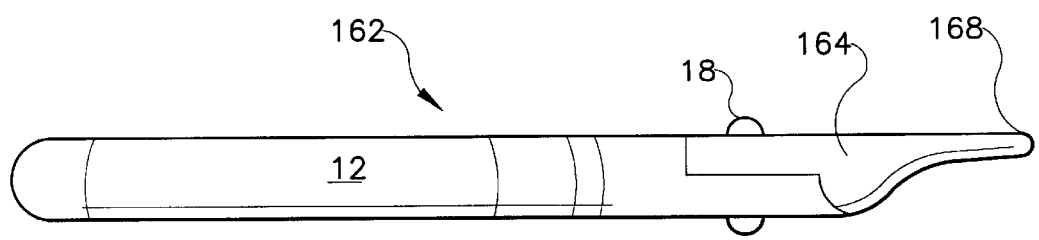
FIG. 17B is a top plan view of the pliers of the fourteenth embodiment.
Figure 17C:
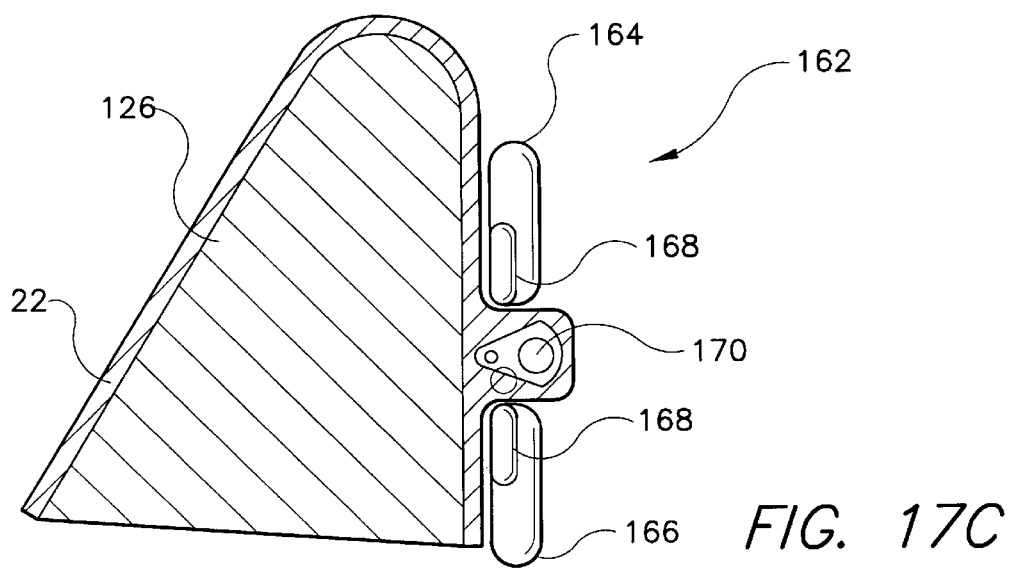
FIG. 17C is a sectional view of a retainer with an expansion screw being crimped by the heated dolphin beak pliers in a direction adjacent to the retainer in the fourteenth embodiment.

FIGS. 17A, 17B, and 17C are directed to a fifteenth embodiment of a crimping pliers 162. In FIG. 17A, the pliers 162 have a first top jaw 164 and a second bottom jaw 166 of equal length and both jaws shaped like a dolphin's nose with aligned narrow beaks 168. The first top jaw 164 has a first handle 10. The second top jaw 166 has a second handle 12 joined to the first handle 10 by a pivot pin 18. FIG. 17B shows a top view of the pliers 162 with the aligned narrow beaks 168. FIG. 17C depicts the crimping action of the heated pliers 162 sealing the thermoplastic retainer 22 on a lower tooth 126 at the location of an expansion screw 170 or the like. It should be noted that the beaks 168 are placed adjacent the retainer 22 for maximum crimping benefit.

Figure 19:
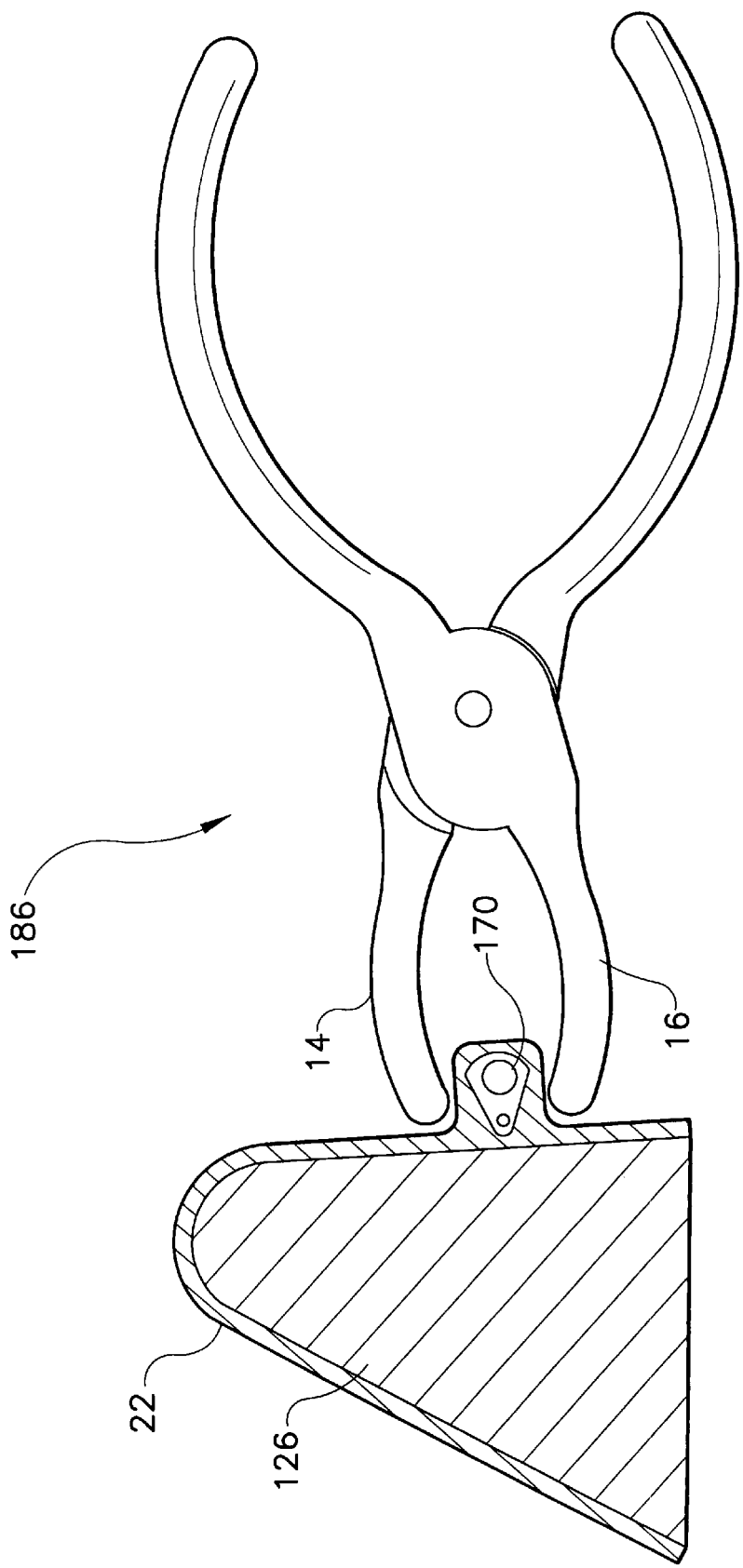
FIG. 19 is an elevational side view of an alternative crimping pliers positioned perpendicular to a retainer in a sixteenth embodiment, wherein a partially sectioned retainer encapsulates an expansion screw on a tooth.

FIG. 19 illustrates an alternative to the crimping of an encapsulated expansion screw 170 or the like by crimping perpendicular to the surface of the retainer 22 on a tooth 126 with the heated crimping pliers 186 as a sixteenth embodiment. In this embodiment, the first and second jaws 14, 16, respectively, are equal in length and similar in having an arcuate shape.

Figure 18A:
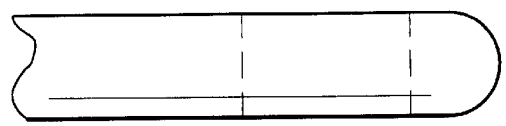
FIG. 18A is a partial side view of the pliers' jaws for forming a bleaching pocket in a retainer of pliers of a fifteenth embodiment. The pliers is capable of utilizing blocks of various sizes.
Figure 18A:
Figure 18B:
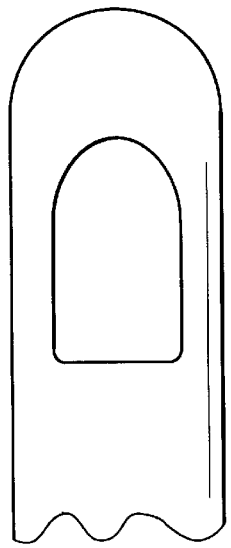
FIG. 18B is a partial plan view of the female jaw's underside of the pliers of the fifteenth embodiment.
Figure 18C:
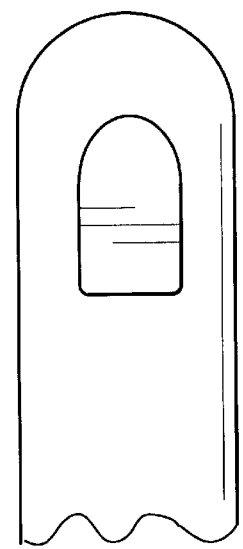
FIG. 18C is a partial plan view of the underside of the male jaw of the pliers of the fifteenth embodiment.
Figure 18D:
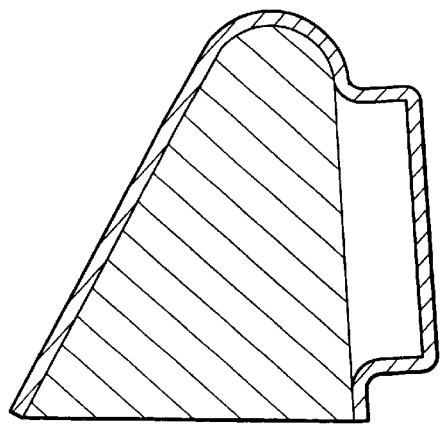
FIG. 18D is a sectional view of a retainer on a tooth with the bleaching pocket formed by the pliers of a seventeenth embodiment.

FIGS. 18A, 18B, 18C, and 18D are directed to a seventeenth embodiment of a bleaching pocket forming pliers 172 for placing bleaching chemicals in the pockets 174 of a retainer 22 to bleach a tooth 126 to a lighter color. The pocket 174 should be approximately the size of the tooth being bleached. Therefore, the male projection of the first jaw 14 (FIG. 18C) should be approximately the size of the tooth being treated (FIG. 18D) in order to avoid unbleached areas being present. Consequently, as seen in FIG. 18A, an interchangeable block 176 of adequate size can be held by a screw 178 in the socket 180 of the first jaw 14. The throughbore 182 of the second jaw 16 (FIG. 18B) can accommodate a certain tolerance in the size differences of the interchangeable block 174. The rounded edge 184 of the block 176 coincides with the gum line for accurate bleaching.

Thus, the present invention of an assortment of bump forming and reforming heated pliers utilized by an orthodontist can economically form various configured and sized bumps to modify a thermoplastic retainer for a better fit to the teeth of a patient.

It is to be understood that the present invention is not limited to the embodiments described above, but encompasses any and all embodiments within the scope of the following claims.

I claim:

1. An orthodontic pliers for forming pockets in a thermoplastic retainer, said orthodontic pliers comprising:

a first component and a second component subapically joined by a pivot pin, said first component having a first handle and a first jaw, and said second component having a second handle and a second jaw;

said first jaw being shorter in length than said second jaw, said first jaw having a projection in the shape of a tooth with a circular shaped top portion; and said second jaw having a corresponding tooth-shaped throughbore;

whereby upon heating the first and second jaws of the pliers and closing the pliers upon a thermoplastic retainer, a tooth-shaped pocket is formed on the thermoplastic retainer for subsequent insertion of fluoride in the pocket.

2. An orthodontic pliers for forming bumps in a thermoplastic retainer, said orthodontic pliers comprising:

a first component and a second component subapically joined by a pivot pin, said first component having a first handle and a first jaw, and said second component having a second handle and a second jaw;

said first jaw and said second jaw each having a longitudinal axis, said first jaw being shorter in length than said second jaw, said first jaw having an end bent at a right angle with an elongated projection attached thereto, said elongated projection being perpendicular to the longitudinal axis of said first jaw; and said second jaw having a corresponding elongated throughbore perpendicular to its longitudinal axis;

whereby upon heating the first and second jaws of the pliers and closing the pliers upon a thermoplastic retainer, a pair of horizontally positioned bumps is formed on the thermoplastic retainer, the pair of bumps being subsequently cut on their outside edges for attachment of bands.

3. An orthodontic pliers for forming bumps in a thermoplastic retainer, said orthodontic pliers comprising:

a first component and a second component subapically joined by a pivot pin, said first component having a first handle and a first jaw, and said second component having a second handle and a second jaw;

said first jaw and said second jaw each having a longitudinal axis, said first jaw being shorter in length than said second jaw, said first jaw having an end bent at a right angle with an elongated projection attached thereto, said elongated projection being aligned along the longitudinal axis of the first jaw; and said second jaw having a corresponding elongated throughbore aligned along its longitudinal axis;

whereby upon heating the first and second jaws of the pliers and closing the pliers upon a thermoplastic retainer, a pair of vertically positioned bumps is formed on the thermoplastic retainer, the pair of bumps being subsequently cut on their upper edges for attachment of bands.

4. An orthodontic pliers for forming bumps in a thermoplastic retainer, said orthodontic pliers comprising:

a first component and a second component subapically joined by a pivot pin, said first component having a first handle and a first jaw, and said second component having a second handle and a second jaw;

said first jaw being shorter in length than said second jaw, said first jaw having a rectangular projection; and said second jaw having a corresponding rectangular throughbore;

whereby upon heating the first and second jaws of the pliers and closing the pliers upon a thermoplastic retainer, a row of rectangular bumps is formed in the thermoplastic retainer, wherein each of the bumps contain a block with an aperture extending through each block and each bump for attachment of orthodontic fasteners.

\* \* \* \* \*